United States Patent [19]

Chutter

[11] 4,275,735
[45] Jun. 30, 1981

[54] SURGICAL BLADE HOLDER

[76] Inventor: Reinald J. Chutter, 1260 Southfield Pl., Virginia Beach, Va. 23452

[21] Appl. No.: 40,912

[22] Filed: May 21, 1979

[51] Int. Cl.³ .............................................. A61B 17/32
[52] U.S. Cl. ...................................... 128/305; 30/329
[58] Field of Search ............... 128/305, 304, 314, 751; 30/334–336, 339, 329, 169, 330, 162, 293, 320, 321; 433/144

[56] References Cited

U.S. PATENT DOCUMENTS

| 42,537 | 4/1864 | Richard | 30/334 X |
|---|---|---|---|
| 1,369,581 | 2/1921 | Vercoutere | 30/293 |
| 2,307,411 | 1/1943 | Leatherman | 30/334 X |
| 2,684,026 | 7/1954 | Randolph | 30/329 X |
| 3,626,592 | 12/1971 | Cas et al. | 30/339 |
| 3,990,451 | 11/1976 | Gibbs | 128/305 |

FOREIGN PATENT DOCUMENTS

| 551270 | 2/1943 | United Kingdom | 30/334 |
| 678098 | 8/1952 | United Kingdom | 128/305 |

OTHER PUBLICATIONS

Hu-Friedy Catalog, pp. 36, 38–41, 43.

Primary Examiner—Robert W. Michell
Assistant Examiner—Michael H. Thaler

[57] ABSTRACT

A surgical blade holder characterized by a handle with a hollow head portion at an obtuse angle with the longitudinal axis of the remainder of the handle. The head portion has a first slot for accommodating a blade-retaining ring which is attached to a shank passing through at least the hollow head portion of the handle. Apparatus is associated with the shank to provide relative motion between the hollow head portion and the blade-retaining ring to move such parts into an engaged position and into a disengaged position. The blade-retaining ring has a slot in the anterior portion thereof and the hollow head portion has at least one second slot for holding a surgical blade in a variety of extensions and angles relative to the handle when the blade-retaining ring and hollow head portion are in the engaged position.

1 Claim, 6 Drawing Figures

SURGICAL BLADE HOLDER

FIELD OF THE INVENTION

This invention relates to a surgical blade holder and knife and more particularly, to such a surgical knife for performing surgery in areas of limited access such as gingival surgery.

The surgical blade holder and knife of the present invention is ideally suited for selected surgical procedures where maximum blade control is desired in areas of limited surgical access such as intra-oral surgical procedures and particularly on the gums. However, while the following description will be directed particularly to the use of the invention in oral surgery, it should be understood that the invention is not necessarily limited thereby.

DESCRIPTION OF THE PRIOR ART

Several types of surgical knives are known in the art. There are knives with non-replaceable blades. These knives have the following disadvantages: (1) a separate instrument must be purchased for each blade shape, size, and blade angle combination desired which (2) necessitates stocking a large number of instruments for a wide variety of uses; (3) these knives are difficult to sharpen well; and (4) their handles have to be discarded when their blades wear out, thus increasing the cost of replacement of the blades. Also, there are presently available knives with replaceable blades mounted in the handle in a single, fixed, non-adjustable manner. This type has the advantage of replaceable blades, but the built-in disadvantage of being able to mount them in the handle in only one fixed, predetermined relationship. A third type of presently available knives is a knife with replaceable blades mounted in the handle in a choice of two or more ways. This allows some discretion to be exercised in the choice of the angle, direction, or/and blade extension. All other factors equal, the greater the variety permitted in these areas, the greater is the potential usefulness of the instrument. The range of flexibility of these parameters offered by a single design varies, but in general is quite limited. The disadvantage of each is in its limited variability of blade orientation and extension.

OBJECTS OF THE INVENTION

Accordingly, it is a main object of this invention to provide a surgical blade holder which can securely support replaceable surgical blades in a variety of unique angles and blade lengths primarily for use in intra-oral surgical procedures.

This and other objects will either be pointed out or become apparent from the following description and drawings.

SUMMARY OF THE INVENTION

The above objects are accomplished in one aspect of the invention by a surgical blade holder comprising (a) a handle with a hollow head portion at an obtuse angle relative to the longitudinal axis of said handle;

(b) said hollow head portion having a first slot which is long relative to at least one second short slot through the forward most section of the wall thereof;

(c) a shank fixed in said handle passing through said hollow head portion;

(d) a blade-retaining ring attached to the anterior portion of said shank;

(e) said blade-retaining ring having a slot in the anterior portion thereof for engaging a surgical blade in combination with said second slot in said head; and (f) means associated with said shank to cause relative motion between said hollow head portion and said shank to move said blade-retaining ring into said first slot in said hollow portion to thereby engage and hold a replaceable surgical blade placed in said second slot for surgery in areas of limited surgical access.

In another aspect of the invention, the objects are accomplished by a surgical knife comprising (a) a handle;

(b) a hollow head portion at an obtuse angle relative to the longitudinal axis of said handle;

(c) said hollow head portion having a first long slot relative to at least one second short slot through the forward most section of the wall thereof;

(d) a shank fixed in said handle passing through said hollow head portion;

(e) a blade-retaining ring at the anterior portion of said shank and having a slot in the anterior portion of said ring;

(f) means associated with said shank to cause relative motion between said hollow head portion and said shank to move such parts into an engaged position and a disengaged position; and (g) a replaceable surgical blade placed in said second short slot at the desired blade extension and angular orientation relative to said handle and held in place by the slot in the blade-retaining ring when said ring and head are in the engaged position.

DESCRIPTION OF SPECIFIC EMBODIMENTS

Figure 1:
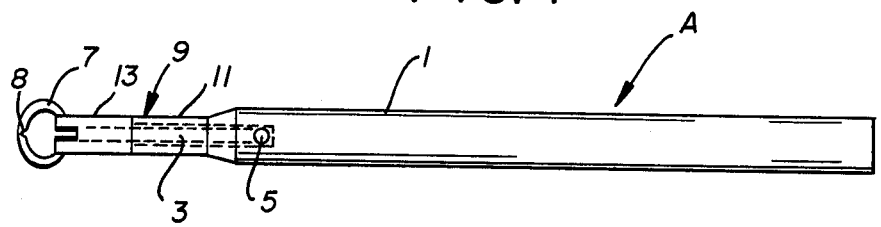
FIG. 1 is a top view of one embodiment of the invention.
Figure 2:
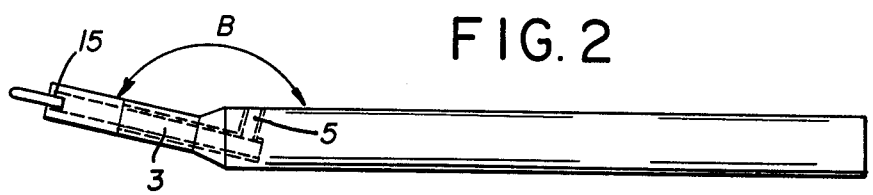
FIG. 2 is a side view of the embodiment of FIG. 1.

Referring now to FIGS. 1 and 2 the blade holder shown generally at A comprises a handle 1, which may be solid or hollow, preferably constructed of stainless steel. A stationary threaded shank 3 oriented at an obtuse angle B to the longitudinal axis of the handle is fixed to the handle 1 as by setscrew 5. The anterior portion of the shank 3 carries a blade-retaining ring 7. The blade-retaining ring 7 has a slot 8 which is preferably "Vee"-shaped. The shank 3 extends from said handle 1 through a hollow head portion shown generally at 9. The hollow head portion consists of knurled and threaded retracting-extension collar 11 which engages the threads of the shank 3 on its inner surface and advances or retracts by rotation. The collar 11 drives or withdraws a non-threaded slotted sleeve 13. The sleeve 13 has a first slot 15 which is long relative to a second slot 17 (see FIGS. 4, 5 and 6) through the forward portion of the wall of the sleeve. The sleeve 13 will respond to movement of the collar 11, which in turn will engage and stabilize the blade 19 in the desired orientation (see FIGS. 4, 5 and 6). The second slot 17 is preferably made of three slots 21, 22, and 23 (see FIG. 6) in an arrowhead configuration. This arrangement gives greater flexibility to blade angle than the single slot shown in FIGS. 1 through 5.

Figure 3:
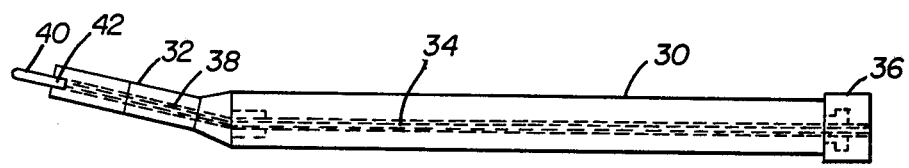
FIG. 3 is a side view of another embodiment of the invention.

Referring to FIG. 3, a blade holder of this embodiment consists of hollow handle 30 with a hollow head portion 32 at an obtuse angle to the longitudinal axis of the handle 30. A retraction-extension rod 34 extends through the entire length of the handle 30 and terminates at the end opposite the head portion and threadably engages a retraction-extension knob 36. The retraction-extension rod 34 has a shank portion 38 extending through the head portion 32 and has attached thereto a blade-retaining ring 40. The head portion 32 has a first slot 42 to receive the blade-retaining ring 40 when the latter is retracted and at least one second slot 17 not visible in FIG. 3 (see FIGS. 4, 5 and 6) shorter than slot 42 to accommodate the surgical blades when they are mounted in place.

Figure 4:
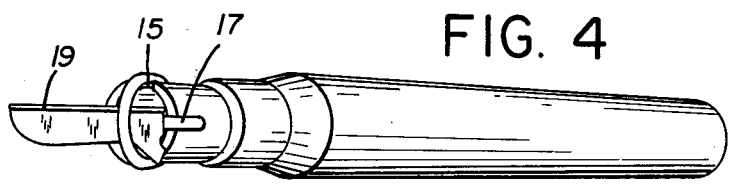
FIG. 4 is a prospective view of the surgical knife of the invention with a replaceable blade in one orientation.
Figure 5:
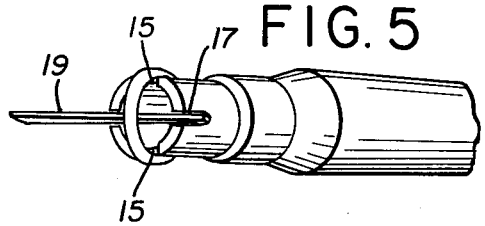
FIG. 5 is a partial prospective view similar to FIG. 4 showing a replaceable blade in another orientation.
Figure 6:
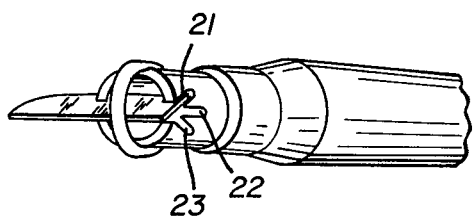
FIG. 6 is a partial prospective view similar to FIGS. 4 and 5 showing the blade in still another orientation when the head of the handle has therein an arrowhead configuration slot arrangement.

In operation, both embodiments of the invention shown are designed to receive a variety of blades presently available. Various modes of blade installation are shown in FIGS. 4, 5 and 6. With the blade oriented relative to the long axis of the handle (FIGS. 5 and 6) incisions lateral to the mandibular posterior teeth are facilitated relative to presently available instruments. With the blade oriented at right angles to the long axis of the blade holder (see FIG. 4) incisions proximal to the posterior teeth are possible. If deeper penetration of the blade is required, greater blade length is provided by appropriate blade selection and mounting. Less extensive requirements for blade penetration in areas where surgical access is restricted can be met by less extensive blade extension during blade installation.

The present invention provides a surgical blade holder which provides unique flexibility in the choice of the blade orientation and blade length previously unavailable to the surgeon. This uniqueness is particularly desirable for intra-oral cutting procedures where surgical access is restricted.

While the invention has been described with reference to certain preferred embodiments and the best mode of operation, it should be understood that certain modifications can be made thereto without departing from the spirit and scope of this invention. For example, the slot configuration can be varied to accommodate various commercial blades. As already mentioned, one or more blade-retaining slots may be used. The slot in the blade-retaining ring may be a "Vee" or a "U"-shaped slot. The pitch of the threads on the threaded shank may be varied to provide better security of blade retention. The outside dimension of the hollow head portion may be varied to provide better observation of the surgical site. Further, the shank 3 shown in the embodiment of FIGS. 1 and 2 may be arranged so that it can be rotated up to ninety degrees to the right or left of its standard position and fixed by setscrew 5 in order to provide still greater flexibility of choice of blade angles relative to the handle.

What is claimed is:

1. A surgical blade holder comprising
(a) a handle with a hollow head portion at an obtuse angle relative to the longitudinal axis of said handle;
(b) said hollow head portion having a first slot which is long relative to three short slots through the forward most section of the wall thereof; one slot of said three short slots having substantially longitudinal orientation with respect to the head portion and the other two slots on either side of said longitudinal slot at essentially 45 degrees relative thereto to form an arrowhead slot configuration;
(c) a shank fixed in said handle passing through said hollow head portion;
(d) a blade-retaining ring attached to the anterior portion of said shank;
(e) said blade-retaining ring having a slot in the anterior portion thereof for engaging a surgical blade in combination with said three short slots in said head; and
(f) means associated with said shank to cause relative motion between said hollow head portion and said shank to move said blade-retaining ring into said first slot in said hollow portion to thereby engage and hold a replaceable surgical blade placed in one of said three short slots for surgery in areas of limited surgical access.

* * * * *